United States Patent [19]
Bonte et al.

[11] Patent Number: 6,004,568
[45] Date of Patent: Dec. 21, 1999

[54] COSMETIC OR PHARMACEUTICAL, PARTICULARLY DERMATOLOGICAL, COMPOSITION CONTAINING A BERTHOLLETIA EXTRACT

[75] Inventors: Frederic Bonte; Marc Dumas, both of Orléans; Catherine Lavaud, Tinqueux; Georges Massiot, Reims, all of France

[73] Assignee: LVMH Recherche, Nanterre, France

[21] Appl. No.: 08/917,622

[22] Filed: Aug. 11, 1997

Related U.S. Application Data

[63] Continuation-in-part of application No. PCT/FR96/00256, Feb. 16, 1996.

[30] Foreign Application Priority Data

Aug. 22, 1996 [FR] France ................................ 96 10356

[51] Int. Cl.⁶ .................................................. A61K 7/00
[52] U.S. Cl. ...................... 424/401; 424/195.1; 514/844; 514/845; 514/474
[58] Field of Search ................................ 424/401, 195.1; 514/844, 474, 845

[56] References Cited

FOREIGN PATENT DOCUMENTS

| 2735982 | 1/1997 | France . |
| 8133952 | 5/1996 | Japan . |
| 9525524 | 9/1995 | WIPO . |

*Primary Examiner*—S. Mark Clardy
*Assistant Examiner*—Michael A. Williamson
*Attorney, Agent, or Firm*—Dennison, Meserole, Scheiner & Schultz

[57] ABSTRACT

The object of the invention is the use of a Bertholletia extract, particularly a Bertholletia excelsa extract, for the preparation of a cosmetic or pharmaceutical composition, particularly a dermatological composition. The Bertholletia extract promotes collagen synthesis or has activity against free radicals, for example to combat the effects of skin ageing, to prevent the formation of wrinkles or reduce their depth, or to promote firmer skin. It also has an activity for promoting the incorporation of vitamin C in the skin cells.

19 Claims, No Drawings

COSMETIC OR PHARMACEUTICAL, PARTICULARLY DERMATOLOGICAL, COMPOSITION CONTAINING A BERTHOLLETIA EXTRACT

This application is a Continuation-in-Part application of the International application PCT/FR 96/00256 filed on Feb. 16, 1996, which in turn claims the priority of French patent application No. 95.01840 filed on Feb. 17, 1995.

BACKGROUND OF THE INVENTION

The present invention relates essentially to a cosmetic or pharmaceutical composition, especially a dermatological composition, containing an extract of Bertholletia.

More precisely, the present invention relates to the use of an extract of Bertholletia as a cosmetic agent or for the preparation of a cosmetic or pharmaceutical composition, especially a dermatological composition, which stimulates collagen synthesis in particular or has anti-free radical activity and which is intended in particular for combating the effects of skin ageing, obtaining firmer skin, improving healing or treating the diverse pathological conditions accompanied by a collagen deficiency, and to cosmetic or pharmaceutical compositions in which said extract is present.

It further relates to novel cell culture media, especially to media for the culture of human skin cells, containing the same extract.

It further relates to cosmetical or pharmaceutical composition promoting the incorporation of vitamin C into skin cells.

The Bertholletia plant belongs to the family of the Lecythidaceae. It is a genus which comprises two extremely similar species: *Bertholletia excelsa* and *Bertholletia nobilis*. These are trees which are found in the tropical regions of South America, particularly in Brazil. They can reach a height of 30 to 40 meters. They are commonly called Brazilian walnut trees or chestnut trees. The nuts of the two species are more or less identical and in practice can be confused with one another. They are used for their nutritional properties.

A description thereof can be found especially in the work "Dictionnaire des Huiles Vegetales" ("Dictionary of Vegetable Oils") by Paul H. Mensier, published by Paul Lechevalier, Paris, 1957.

In Amazonia, the bark of the trunk of Bertholletia excelsa, which contains saponins in particular, is used as an infusion for combating liver diseases. The oil from its nuts can be used for the manufacture of soaps (R. E. Schultes et al., The healing forest. Discorides Press, Portland, Oreg., USA, 1990, vol. 2, pages 225– 226).

SUMMARY OF THE INVENTION

It has now been discovered that extracts of Bertholletia are of great value in cosmetics, especially for skin care.

In particular, a surprising activity of extracts of Bertholletia on the synthesis of collagen, particularly type I, type IV and type VII collagen, hereafter abbreviated to "collagen I", "collagen IV" and "collagen VII", has been discovered.

The skin is known to contain essentially collagen I; this is a protein synthesized by the fibroblasts, which are the most numerous cells in the dermis. This protein plays a supporting role and is responsible for the rheological properties of the dermis, particularly its firmness, and the maintenance of its architecture (E. U. KUCHARZ, "The collagens: Biochemistry and pathophysiology", Springer Verlag, Berlin 1992). It has furthermore been shown that the fibroblasts of the dermis secrete less collagen in the elderly than in the young (M. DUMAS et al., Mech. Ageing Dev. (1994) 73 179–187). Thus ageing is accompanied by a deterioration in the rheological properties of the skin and in its response to the stresses to which it is subjected every day. The skin distends, reacts less well to stretching and loses its tonicity and the wrinkles deepen.

It is also known that collagen IV is a major collagen of the epidermal-dermal junction. Reference may be made on this subject to the article by Briggaman R. A. entitled "Biochemical composition of the epidermal-dermal junction and other basement membrane", published in J. Invest. Dermatol. 78 (1982), pages 1–6, or the article by P. Verando entitled "La jonction dermoépidermique" ("The epidermal-dermal junction"), published by Inserm in Séminaire Inserm, vol. 214, (1991), pages 83–100.

This collagen IV, which is found in the lamina densa, is involved in the cellular attachment and is synthesized by the keratinocytes. The anchoring plates provide the connections between the anchoring fibrils (collagen VII), connected to the keratinocytes, and the fibers of the dermal collagen (collagen I and III). These anchoring plates consist of collagen IV. They are essential in the maintenance of a functional interface between the two skin compartments. Collagen IV also plays an important role in healing processes, enabling the formation of good-quality scar tissue.

Type VII collagen is the predominant constituent of the anchoring fibrils, associated with the basement membrane, connecting the epidermis to the dermis. It is synthesized by the basal keratinocytes and, to a lesser extent, by the fibroblasts of the dermis, as described by R. BURGESON, "Type VII collagen, anchoring fibrils, and epidermolysis bullosa", J. Invest. Dermatol., 101, 252–255, 1993. Recent studies have shown that a topical application of retinoic acid increases the number of anchoring fibrils on skin which has been subjected to actinic ageing.

According to Y. Q. CHEN, A. MAUVIEL, J. RYYNANEN, S. SOLLBERG, J. UITTO: "Type VII collagen gene expression by human skin fibroblasts and keratinocytes in culture: Influence of donor age and cytokine responses", J. Invest. Dermatol. (1994), 102, (2), 205–209, the manifestations of skin ageing, such as an increase in skin fragility and a decrease in the repair capabilities of the epidermis, might be attributable to a reduction in collagen VII synthesis in the elderly.

It has moreover been discovered that extracts of Bertholletia have remarkable anti-free radical activity, i.e. they act as free radical scavengers. The beneficial effects of free radical scavengers on the skin have recently been mentioned by F. J. Wright in J. Appl. Cosmetol. 13 (1995), pages 41–50.

Now, it is recognized that free radicals are involved in ageing phenomena, particularly in the skin, and modify the qualities and properties of the skin. Reference may be made on this subject to the work by I. Emerit entitled "Free radicals and aging", I. Emerit, B. Chance eds, Birkhauser Verlag, Basle, 1992, pages 328–341.

The action of extracts of Bertholletia on collagen synthesis or on free radicals therefore makes them particularly useful for combating the effects of skin ageing, such as wrinkles or the relaxation of the basal tissues of the skin, or for improving healing.

It has also been demonstrated, totally surprisingly, that an extract of Bertholletia has an effect on the secretion of collagen VII by a strain of normal human keratinocytes in culture.

This finding has led to the development of novel cosmetic or pharmaceutical compositions, especially dermatological compositions, which are more particularly useful in all applications where it is desired to stimulate collagen VII synthesis, especially with a view to promoting the epidermal-dermal cohesion. This property has proved particularly useful for the development of topical cosmetic or dermatological compositions. Such compositions make it possible in particular to promote the epidermal-dermal cohesion in relaxed skin which lacks tonicity. They also make it possible to treat pathological conditions in which the epidermal-dermal junction is deficient, such as epidermolysis bullosa.

Furthermore, it has also been shown that, surprisingly, extracts of Bertholletia make it possible considerably to improve the incorporation (or transport) of vitamin C into the skin cells, particularly the fibroblasts.

Now, it was known that vitamin C or L-ascorbic acid was involved at different levels in mammalian cells:

as an antioxidant by virtue of its low redox potential, particularly in the mechanisms of cell protection against the peroxides continually produced by the mitochondrial respiratory chain, and as a cofactor for enzymes such as the hydroxylases essential for the synthesis of type I and III collagens.

Thus vitamin C is of great importance in several of the cell's vital functions, which explains the interest taken in its transport from the extracellular medium to the cytoplasmic compartment. Now, this molecule is not synthesized by human cells, especially skin cells. It is provided by food, which is absorbed in the intestine and transported into all the tissues by the blood, in which the plasma level generally reaches about 25 $\mu$M. It is incorporated into the cell against the protein concentration gradient by a high affinity protein transporter.

The latter finding has made it possible to develop novel cosmetic or pharmaceutical compositions, especially dermatological compositions, which are more particularly useful in all applications where it is desired to improve the incorporation of vitamin C into the skin cells, particularly into the fibroblasts.

One main object of the present invention is therefore to solve the novel technical problem which consists in providing a novel formulation of cosmetic or pharmaceutical composition, especially dermatological composition, which is effective in preventing or treating the effects of skin ageing and in firming the skin, or for improving healing, for improving the dermal-epidermal cohesion, or which is effective against free radicals or for promoting incorporation of vitamin C by skin cells.

Another main object of the present invention is to solve this novel technical problem in a particularly simple and satisfactory manner which can be utilized on the industrial scale, especially in the cosmetics or pharmaceuticals industry.

DETAILED DESCRIPTION OF THE INVENTION

Thus, according to a first feature, the present invention relates to the use of an extract of Bertholletia as a cosmetic agent, especially with anti-free radical activity, in particular for skin care.

In one embodiment of the invention, an extract of Bertholletia, particularly *Bertholletia excelsa*, is used for the preparation of a cosmetic or pharmaceutical composition, especially a dermatological composition, which stimulates especially the synthesis of collagen, particularly collagen I or collagen IV, or collagen VII, has anti-free radical activity, and which is intended especially for improving skin healing as well as the biomechanical properties and surface appearance of the skin, obtaining firmer skin, combating the effects of skin ageing or treating the diverse pathological conditions accompanied by a collagen deficiency.

In one advantageous embodiment, the extract of Bertholletia is used for the preparation of a composition which is effective against skin ageing, particularly against wrinkles, and which is intended for preventing the appearance of wrinkles or reducing their depth.

In another embodiment, the extract of Bertholletia is an extract of the bark of this plant, particularly an extract of the trunk of the *Bertholletia excelsa* plant.

In another embodiment, the extract of Bertholletia is an extract of the fruits, i.e. the nuts, of Bertholletia, preferably extracts of the pericarp of the nuts of Bertholletia, and particularly preferably *Bertholletia excelsa*.

In particular, the extract of Bertholletia can be obtained by the process described below by way of indication, but without implying a limitation.

A first extraction is carried out on the bark or the nuts of the plant, particularly the bark of the trunk or the pericarp of the nuts, with a polar solvent advantageously selected from the group comprising water, alcohols preferably containing from 1 to 4 carbon atoms, chlorinated solvents preferably containing 1 or 2 carbon atoms, organic esters preferably containing from 3 to 6 carbon atoms, and a mixed solvent based on any mixture of the above-mentioned solvents.

Particularly preferably, the first extraction solvent is selected from the group consisting in water, methanol, ethanol, methanol/water mixtures, ethanol/water mixtures, chloroform and dichloromethane and their mixtures. Particularly preferably, the solvent is water, methanol, ethanol or any mixture of these solvents.

The ratio of the bark or the nuts, particularly the pericarp of the nuts, to the extraction agent is not critical and will generally be between 1:5 and 1:20 parts by weight.

The extraction is generally carried out at temperatures between room temperature and the boiling point of the solvent used for the extraction.

This first extraction is preferably carried out under reflux at atmospheric pressure for a period of 2 to 4 h. It is also advantageously preceded by a cold maceration for 2 to 4 h in the extraction solvent.

When extraction is complete, the solvent phase containing the extract is filtered and then concentrated and/or evaporated to dryness under reduced pressure to give a first crude extract of Bertholletia according to the invention. This crude extract can be purified by various processes well known to those skilled in the art.

The extracts of Bertholletia, more particularly *Bertholletia excelsa*, are rich in saponins. Also, these extracts, particularly the extracts of the pericarp of the nuts of *Bertholletia excelsa*, contain tannins, particularly ellagotannin and gallotannins, irrespective of the polar extraction solvent used, such as water or methanol.

In particular, if it is desired to enrich the extract of Bertholletia according to the invention in saponins, the process described below by way of indication, but without implying a limitation, is used. The extract obtained after the first extraction is evaporated to dryness. The residue is then taken up with methanol. The solution obtained is poured into acetone. The precipitate which then forms is recovered by filtration. Preferably, this precipitate is dried and then dialyzed against demineralized water. Finally, the product is lyophilized to give a dry extract of Bertholletia enriched in saponins, according to the invention.

The extraction processes described above apply in particular to the species *Bertholletia excelsa*.

According to a second feature, the present invention further relates to a cosmetic composition characterized in that it comprises, as the active ingredient, a cosmetically effective amount of an extract of Bertholletia, particularly *Bertholletia excelsa*, preferably dispersed in a cosmetically acceptable excipient.

In one particular embodiment, this cosmetic composition which stimulates the synthesis of collagen, particularly collagen I or collagen IV, or which has anti-free radical activity, is intended especially for combating the effects of skin ageing or for obtaining firmer skin. For example, such a composition can advantageously be used as a composition for preventing the appearance of wrinkles or reducing their depth.

According to another embodiment, the invention relates to the use of an extract of Bertholletia, particularly *Bertholletia excelsa*, as a cosmetic agent for stimulating collagen VII synthesis.

This cosmetic agent will be introduced into a cosmetic composition comprising a cosmetically acceptable vehicle, in which the extract will be dissolved or suspended.

According to this feature, where the action of the cosmetic agent is to promote collagen VII synthesis, the composition will prove particularly useful in all applications where it is desired to improve the epidermal-dermal cohesion. This may involve in particular an anti-wrinkle product or a product for combating actinic ageing of the skin, i.e. ageing induced by radiation, particularly ultraviolet solar radiation.

In general terms, according to this feature, the cosmetic compositions of the invention prove particularly useful as skin-firming products, particularly for combating loose skin or skin which lacks tonicity.

According to another embodiment of the present invention, the extract of Bertholletia is used for promoting the incorporation of vitamin C into the skin cells, particularly into the fibroblasts.

According to this latter embodiment, the cosmetic compositions are intended for improving the incorporation of vitamin C by the skin cells. Such an effect will lead to an improvement in the cell metabolism, particularly to a stimulation of the cellular syntheses, especially those of the different types of collagen and elastin. Thus, by promoting the incorporation of vitamin C, extracts of Bertholletia, particularly *Bertholletia excelsa*, improve the condition of the skin, especially by restoring or increasing its tonicity and its elasticity and by delaying the appearance of wrinkles.

In one embodiment of one or other of these two above embodiments, said cosmetic agent is incorporated into a composition for topical use which also contains vitamin C or an ascorbic acid derivative. According to a third feature, the invention further relates to a pharmaceutical composition, especially a dermatological composition, which stimulates the synthesis of collagen, particularly collagen I or collagen IV, or which has anti-free radical activity, said composition being characterized in that it comprises, as the active ingredient, a pharmaceutically effective amount of an extract of Bertholletia, particularly *Bertholletia excelsa*, dispersed in a pharmaceutically acceptable excipient.

In one particular embodiment, said composition is intended for improving skin healing or treating the diverse pathological conditions which are accompanied by a collagen deficiency or result from the presence of free radicals.

The invention further relates to the use of the same extracts of Bertholletia for the preparation of a pharmaceutical composition for treating pathological conditions associated with a deficiency of the epidermal-dermal junction, particularly those associated with a deficiency of collagen VII synthesis.

Epidermolysis bullosa may be mentioned in particular as an example of such pathological conditions.

In another embodiment of the invention, the extract of the Bertholletia plant will be used for the preparation of a pharmaceutical composition, especially a dermatological composition, for treating pathological conditions associated with a deficiency of vitamin C incorporation into the skin cells, particularly into the fibroblasts.

The above pharmaceutical composition will advantageously contain a pharmaceutically acceptable vehicle, in which the extract of Bertholletia will be dissolved or suspended.

In one particularly advantageous embodiment, it will also contain vitamin C or an ascorbic acid derivative. The effect of the extract of Bertholletia in such a composition will be to improve the incorporation of vitamin C into the cells which are deficient in said compound.

According to a fourth feature, the invention also covers a method of cosmetic or pharmaceutical treatment, especially dermatological treatment, characterized in that it comprises the application of an amount of an extract of Bertholletia, especially *Bertholletia excelsa*, particularly dispersed in a cosmetically or pharmaceutically acceptable excipient, said amount being cosmetically or pharmaceutically effective for a cosmetic or pharmaceutical treatment. Said application is preferably a topical application to areas of the skin in question. The cosmetic or pharmaceutical applications which are particularly advantageous at the present time result from the foregoing description and the following description relating to the Examples, and from the claims. The same applies to the extract concentration.

In one or other of the above features, the extract of Bertholletia, particularly *Bertholletia excelsa*, will preferably be used at a concentration of between 0.0001% and 1% by weight, based on the total weight of the final composition. This concentration is preferably between 0.01% and 0.25% by weight, based on the total weight of the final composition.

Again, in any one of the above features, the composition according to the invention preferably also contains an active substance selected from the group comprising ascorbic acid, madecassic acid, asiatic acid, madecassoside, asiaticoside, alpha-1-proteinase inhibitor, collagenase inhibitors such as retinoic acid, elastase inhibitors, lysine, proline, 2-oxoglutarate and ginsenoside $R_0$.

The composition may also contain vitamin D and its derivatives, ecdysteroids, particularly beta-ecdysone, and vitamin E.

Finally, according to a last feature, the invention further relates to a method of treating cells in culture, particularly human skin cells, especially fibroblasts and keratinocytes, with an effective concentration of an extract of Bertholletia in order to stimulate collagen, particularly collagen I, IV and VII, synthesis or improve the incorporation of vitamin C into said cells.

The above-mentioned method of treating cells in culture, according to the invention, is particularly advantageous when it is applied in the case of the preparation of reconstituted skin. When immobilized on a substrate, said cells reconstitute an extracellular matrix more rapidly and the appearance of an epidermal-dermal junction is promoted.

In one preferred mode of carrying out this method, the cell culture is treated with an extract of Bertholletia at a concentration of between 0.1 µg/ml and 10 µg/ml, based on the culture medium.

Other objects, characteristics and advantages of the invention will become clearly apparent from the following explanatory description referring to several Examples, which are given solely by way of illustration and which cannot consequently limit the scope of the invention in any way.

In the Examples, the percentages are expressed by weight unless indicated otherwise. The amounts of the extracts are expressed by dry weight.

EXAMPLE 1

Preparation of a Methanolic Extract of the Bark of the Trunk of *Bertholletia excelsa*, Enriched in Saponins Powdered bark of the trunk of *Bertholletia excelsa* is prepared by grinding. 49 g of this powder are then macerated for 2 h in 500 ml of methanol. The whole mixture is refluxed for 3 h and then left to cool and filtered on a glass frit. The filtrate obtained constitutes a first extract according to the invention, called extract $I_1$. This first extract is evaporated to dryness. The residue, weighing 14.7 g, is taken up with 100 ml of methanol. This solution is poured into 500 ml of acetone to give a precipitate, which is then filtered off. The precipitate is subsequently dried over a solid dehydrating agent, such as potassium hydroxide, to give 1.33 g of dry product. 830 mg of this product are subsequently dialyzed for 4 days against 9 ml of demineralized water and then lyophilized to give 182 mg of saponin-enriched extract according to the invention, called extract $I_2$.

EXAMPLE 2

Preparation of a Methanolic Extract of the Pericarp of Nuts of the Brazilian *Bertholletia excelsa*, Enriched in Saponin The pericarps of nuts of the Brazilian *Bertholletia excelsa*, which are commercially available, are collected and ground coarsely and finely.

100 g of the resulting powdered nut pericarp are then extracted three times in succession with 1 l of methanol under reflux for 30 min.

Each extract is filtered on a filter of pore diameter 0.45 µm and the three extracts are combined.

The combined extracts are concentrated on a rotary evaporator until a dry film is obtained.

This film is taken up by shaking with water. The resulting milk is lyophilized.

This gives about 5 g of saponin-enriched extract of nut pericarp according to the invention, called extract $I_3$. It will be noted that the yield of the extraction is of the order of 5%.

EXAMPLE 3

Demonstration of the Activity of a Methanolic Extract of the Bark of *Bertholletia excelsa*, Prepared According to Example 1, Extract $I_2$, on Collagen I Synthesis by Human Fibroblasts in Culture Culture of Fibroblasts Cultures of fibroblasts of healthy adult dermis are prepared by the explant method using a sample of facial skin obtained from a 60-year-old woman in the course of a face-lift.

The fibroblasts are cultivated to the point of confluence in an E 199 medium (Gibco) supplemented with 2 mmol/l of L-glutamine (Gibco) and 10% v/v of fetal calf serum (Gibco) at 37° C. in a humidified atmosphere containing 5% of $CO_2$. For evaluation of the collagen content, the primary cultures in confluence are harvested with a solution containing 0.1% of trypsin and 0.02% of EDTA in phosphate buffered saline (PBS) at pH 7.2 and the cells are then inoculated, at a density of $10^4$ fibroblasts per well, into 96-well microculture plates (Falcon) in the presence of the same culture medium as that described above.

24 h after inoculation, the medium is removed and replaced with a medium of the same composition as the medium described above, except that it does not contain serum and that 25 µmol/l of L-ascorbic acid in the form of the sodium salt have been added. Moreover, this new medium may or may not contain the test product (extract $I_2$), depending on whether it is a treated culture or a control culture. Incubation is then carried out for an additional period of 48 h at 37° C. The test product (extract $I_2$) has been dissolved in DMSO before incorporation into the culture medium (the final concentration of DMSO in the medium is 0.1% v/v).

Viability of the Cells

At the end of the incubation period, the medium is removed and an MTT cell viability test was performed according to the publication by Denizot F. et al., J. Immunol. Methods, (1986) 89, 271–277. The cells are incubated with 100 µl of a solution containing 0.5 mg/ml of tetrazolium salt (3-[4,5-dimethylthiazol-2-yl]-2,5-diphenyltetrazolium bromide or MTT) in E 199 medium without phenol red (Gibco) for 3 h at 37° C. 100 µl of isopropanol are then added to each well in order to solubilize the dark-colored formazan blue derivative formed by the living cells. The absorbance is measured at 540 nm.

Measurement of the Collagen

The total amount of type I collagen secreted by the fibroblasts, which is found either associated with the cells or released into the serum-impoverished medium after incubation for 48 h with or without the product (extract $I_2$), is determined by an ELISA test as previously described in the publication by Dumas M. et al., Mech. Ageing Dev. (1994) 73 179–187, and the publication by Grimaud J. P. et al., in: Methods of Enzymatic Analysis (Bermeyer, H. U., ed.), VCH Publishers, Weinheim, (1986), 186–201.

The serum-impoverished incubation media and the residual cells, homogenized by sonication in ice, are collected and transferred to the wells of a plastic immunotiter plate (NUNC) for a 24 h incubation at +4° C. to allow the secreted collagen to adhere. Protease inhibitors (ethylmaleimide, phenylmethylsulfonyl fluoride and ethylenediaminetetraacetate, each in a final concentration of 1 mM) are added during this period. The plates are then rinsed with PBS. A similar washing step is carried out after each plate treatment.

After incubation for 24 h at 4° C. with serum albumin to prevent non-specific binding, anti-human type I collagen rabbit antibodies (Institut Pasteur, Lyon, France) are added for 1.5 h at 22° C. and the bound antibodies are reacted with anti-rabbit goat IgG combined with alkaline phosphatase (Interchim, Montluçon, France). The absorbance of the paranitrophenol formed from paranitrophenyl phosphate (Sigma) by the alkaline phosphatase is measured at 405 nm. The optical densities are converted to nanograms of collagen using a calibration curve established with purified human type I collagen (Institut Jacques Boy, France).

Statistics

The amounts of collagen (mean±SD, standard deviation, n=6) are compared with those determined on the untreated control cultures. The significance of this comparison is assessed for values of p below 0.05 by the Student t test.

Results

The percentage stimulation A of collagen I synthesis is calculated by comparing the amounts of collagen I secreted in the control cultures (without any test product), $C_o$, and in the treated cultures, $C_t$, on the basis of the following formula:

$$A = \frac{C_t - C_o}{C_o} \times 100$$

The results are collated in Table I below.

TABLE I

| Culture | % viability/ control | Collagen I secreted by fibroblasts (ng/10,000 cells/48 h) | % stimulation A | Significance |
|---------|----------------------|-----------------------------------------------------------|-----------------|--------------|
| Control culture without product | 100 | 924 | 0 | |
| Product of the invention $I_2$ at 1 µg/ml | 100 | 1359 | +47 | S* |
| Product of the invention $I_2$ at 2.5 µg/ml | 100 | 2163 | +134 | S* |

*S = significant

An examination of Table I shows first of all that the percentage viability of the cells in the treated cultures has not varied significantly compared with that of the control cultures. The extract $I_2$ therefore exhibits no cytotoxicity.

In this Table the amounts of collagen I secreted by the fibroblasts have been expressed in ng/10,000 cells/48 h.

It will be observed from Table I that the methanolic extract of *Bertholletia excelsa* has produced a significant stimulating activity on collagen I synthesis by the fibroblasts.

Thus the extract of *Bertholletia excelsa* can be used for products which are intended for combating skin ageing or which require an increase in local collagen synthesis, as is the case of a wrinkle treatment, or for contributing to an improvement in skin healing.

EXAMPLE 4

Demonstration of the Activity of a Methanolic Extract of the Pericarp of Nuts of *Bertholletia excelsa* According to the Invention, Extract $I_3$, on Collagen IV Synthesis by Human Keratinocytes in Culture Culture of the Keratinocytes Human keratinocytes originating from a face-lift on a 60-year-old woman with caucasian skin are cultivated in a Gibco keratinocyte-specific growth medium, SFM-K, complemented with EGF (epidermal growth factor) and pituitary extract (Gibco, France). The cells are inoculated into this SFM-K medium at a rate of 30,000 per culture well.

After 24 h the inoculation medium is withdrawn and replaced with SFM-K medium diluted to 1/50 in the same base medium but without EGF and pituitary extract. The test product (dissolved in DMSO) will then be added at the different concentrations for 48 h. The control cultures will receive the same amount of solvent for the test product, in this case DMSO (final concentration 0.1%).

The culture supernatants are recovered and the collagen IV is assayed by a conventional ELISA technique previously described in Dumas M. et al., Mechanisms of Ageing and Development, 73, 1994, pages 179–187. The anti-human collagen IV antibody used is supplied by the Institut Pasteur, Lyon, France.

At the same time an overall assay of the proteins is performed by the bicinchoninic acid technique using a BCA kit marketed by Sigma, France.

The results obtained are reported in Table II below:

TABLE II

| PRODUCT | Collagen IV ng/100 µg of proteins | Percentage activity | Significance |
|---------|-----------------------------------|---------------------|--------------|
| DMSO control | 1.499 ± 0.635 | | |
| Product of the invention $I_3$ at 1 µg/ml | 2.983 ± 0.613 | +99 | S* |
| Product of the invention $I_3$ at 10 µg/ml | 3.153 ± 0.732 | +110 | S* |

*S = significant at the 5% level

An examination of Table II shows very clearly that the test extract significantly stimulates collagen IV synthesis by the human keratinocytes in culture. One of its applications is therefore to strengthen the structure and properties of the epidermal-dermal junction, an exchange zone between the dermis and the epidermis and a very important zone for the keratinocyte differentiation processes.

EXAMPLE 5

Demonstration of the Anti-free Radical Activity of a Methanolic Extract of the Pericarp of Nuts of *Bertholletia excelsa*

The extract 13 of Example 2 is used in this experiment. This test is based on measurement of the cellular viability of normal human keratinocytes subjected to free radical aggression by a hypoxanthine/xanthine oxidase or HX/XO system.

This increase in cellular viability with and without product in the cultures will be evaluated by a method comparable to that described by M. S. NoN1-Hudson et al. in International Journal of Cosmetic Science 1990, 12, pages 105–114, which is incorporated here in its totality by way of reference.

Test Protocol

Preputial keratinocytes are cultivated in a K-SFM medium from Gibco, France, complemented with EGF and bovine pituitary gland extracts. The medium is changed every other day until confluence is reached.

After trypsinization the cells are introduced into 96-well dishes at a concentration of 20,000 cells per well. They are then left to proliferate in K-SFM medium for 2 days.

The HX/XO system (Sigma, France) is added to a Hanks' solution, pH 7.4, and used at concentrations of 8 mU XO/ml and 80 µg hypoxanthine/ml.

The HX/XO system is added after the cells have been washed, left in contact with the cells for 150 min and then stopped by emptying the wells and rinsing the cells.

The viability with and without product is measured by an MTT colorimetric test as described in Example 3 above.

The test product, namely the extract $I_3$ of Example 2, is administered at 1.25 µg/ml and 5 µg/ml in DMSO for 48 h before the oxidative stress of HX/XO and during the stress.

The results obtained are listed in Table III below.

TABLE III

| Product | Cellular viability without HX/XO | Cellular viability with HX/XO | Significance |
|---|---|---|---|
| Control | 100% | 40% | |
| Extract $I_3$ of the invention at 1.25 µg/ml | 100% | 56% | S* |
| Extract $I_3$ of the invention at 5 µg/ml | 100% | 81% | S* |

*S = significant at the 5% level

Table III clearly shows that:
a) under the experimental conditions, the HX/XO system kills 60% of the cells, only 40% remaining viable;
b) at 1.25 µg/ml the extract $I_3$ of the invention already protects the keratinocytes strongly from the toxic effect of the HX/XO system, 56% of the cells surviving the aggression, compared with 40% in the control cultures, so this protection is significant and thus demonstrates the anti-free radical property of the extract $I_3$ according to the invention;
c) at 5 µg/ml this effect is all the more significant because 81% of the cells survive, compared with 40% in the control.

Thus it can be seen that the extracts of Bertholletia according to the invention allow a remarkable percentage of cells to survive aggression, clearly demonstrating the anti-free radical properties of these extracts and their value for skin care.

Thus, by virtue of their property of stimulating collagen synthesis, the extracts of *Bertholletia excelsa* can advantageously be used as the active agent in cosmetic or pharmaceutical compositions, especially dermatological compositions, as defined above.

Various formulations of cosmetic compositions are given below:

EXAMPLE 6
Skin-firming Massage Gel

Extract of *Bertholletia excelsa* bark $I_2$ of Example 1 0.1 g

Ethanol 5 g

Glycerol 2 g

Propylene glycol 2 g

Carbopol 940® 1.25 g

Aqueous excipient with preservative and optionally perfume qsp 100.00 g

Part of the aqueous excipient is used with the Carbopol for the separate preparation of a gel; the other part of the aqueous excipient is used for mixing with the other components and the gel is added to the resulting solution to give a gelled composition forming the massage gel.

This massage gel composition can be used on the bust three times a week for two months.

EXAMPLE 7
Skin-firming Body Care Lotion

Extract of *Bertholletia excelsa* bark $I_1$ of Example 1 0.5 g

Ethanol 1 g

Hyaluronic acid 0.5 g

Aqueous excipient containing a preservative and optionally a perfume qsp 100.00 g The extract is first solubilized in the solubilizing agent and is then added to the aqueous excipient, to which the hyaluronic acid is added.

The lotion obtained can be used in a three-week course of treatment on the areas sensitive to relaxation, such as the abdomen and the thighs.

EXAMPLE 8
Anti-wrinkle Emulsion

Extract of *Bertholletia excelsa* bark $I_2$ of Example 1 0.025 g

Perfumed emulsified excipient qsp 100.00 g

EXAMPLE 9
Healing Composition

Extract of *Bertholletia excelsa* bark $I_1$ of Example 1 0.5 g

Emulsified excipient of the water-in-oil type qsp 100.00 g

EXAMPLE 10
Skin-firming Beauty Cream

Extract of *Bertholletia excelsa* trunk bark $I_2$ of Example 1 0.1 g

Asiaticoside 0.05 g

Ascorbyl phosphate (magnesium salt) 0.1 g

Proline 0.05 g

Emulsified excipients with preservative qsp 100.00 g

Applied once or twice a day in a three-week course of treatment, this cream restores the properties of firmness and elasticity and the radiance of young skin.

EXAMPLE 11
Anti-ageing Cream

Extract of *Bertholletia excelsa* nut pericarp $I_3$ of Example 2 0.2 g

Magnesium ascorbate phosphate 1 g

Hyaluronic acid 1 g

Perfumed emulsified excipient with preservative qsp 100 g

Applied locally to the neck and the lower part of the face once or twice a day in a 3-week course of treatment, this cream restores the firmness properties, the elasticity and the radiance of young skin.

EXAMPLE 12
Anti-wrinkle Face Care Cream

Extract of *Bertholletia excelsa* nut pericarp $I_3$ of Example 2 0.1 g

Alpha-tocopherol 0.05 g

Vitamin C as the magnesium phosphate salt 0.1 g

Madecassoside 0.1 g

Vitamin A palmitate 0.003 g

Aqueous excipient containing a preservative and optionally a perfume qsp 100.00 g Prepared in conventional manner and applied to facial wrinkles once or twice a day in a 3-week course of treatment, this cream makes it possible to restore the properties of firmness and elasticity and the radiance of young skin by removing or reducing the wrinkles.

EXAMPLE 13
Preparation of an Aqueous Extract

Previously ground nut pericarp is extracted for three times 30 minutes with boiling water and the 3 extracts are combined, filtered on a 0.45 μm filter and lyophilized to give thin, light, brown flakes.

The initial ratio ground drug/solvent is 1/10.

The extraction yield is 8%.

EXAMPLE 14
Demonstration of the Stimulation of Collagen VII Synthesis

The following test was performed on the extract $I_3$ recovered in Example 2.

The tests were performed blind.

1—Test Protocol a) Origin of the Keratinocytes

The cultures of normal human keratinocytes (NHK) are prepared from a surgically removed sample of healthy skin. In the present study, the tests were performed on a cellular strain originating from a face-lift carried out on a 44-year-old caucasian woman (strain denoted by HK 44 years). The results were confirmed on another cellular strain, denoted by HK 56 years, originating from a face-lift carried out on a 56-year-old caucasian woman.

b) Culture Conditions

The keratinocytes are kept in complete serum free medium (denoted by SFMc, GIBCO). The cells were sub-cultivated once from the primary culture (i.e. one pass, denoted by P1).

c) Treatment Conditions

The cells are inoculated into SFMc in a 96-well culture dish at a rate of 30,000 NHK per well. After incubation for 24 h, which is necessary for good adhesion of the cells, the medium is replaced with SFMc diluted to 2%, limiting the proliferation of the keratinocytes. The stock solutions of the product obtained according to Example 2 (denoted by $I_3$ in Table IV) are prepared immediately before use in DMSO at concentrations of 1, 2.5 and 5 mg/ml and are introduced into the test medium at a final concentration of 0.1% v/v (i.e. the test concentrations are 1, 2.5 and 5 μg/ml). The control receives the excipient for the product, i.e. 0.1% v/v of DMSO. Neither the XTT viability test nor microscopic observation of the cells revealed cytotoxic effects of the product at concentrations below 10 μg/ml (BOEHRINGER XTT kit, ref. 1465015).

The cells are brought into contact with the treatment medium for 72 h, which is the time required for optimum collagen VII synthesis according to a prior kinetics study.

The incubation supernatants are removed for assay of the collagen VII secreted. The proteins are assayed on the cellular mat remaining in the wells (BCA method, SIGMA) for the purpose of determining the ratio of the amounts of collagen VII secreted to the amounts of cellular proteins.

Six cultures are prepared for each of the three concentrations and for the control experiment.

d) ELISA Assay of the Collagen VII

The protocol for assaying the collagen VII by an ELISA method was adapted from that used for assaying collagen I (M. DUMAS, C. CHAUDAGNE, F. BONTE, A. MEYBECK: "In vitro biosynthesis of type I and III collagens by human dermal fibroblasts from donors of increasing age". Mechanisms of Ageing and Development, 73 (1994) 179–187).

The following modifications were made:

1st antibody: Anti-human type VII collagen monoclonal mouse antibody, isotype IgG1 (Life Technologies, ref. 12073-011).

2nd antibody: Anti-total mouse IgG goat antibody coupled with alkaline phosphatase (Interchim, ref. 115-056-062).

e) Expression of the Results and Statistical Interpretation

In the absence of commercially available human type VII collagen to establish a calibration range, the results of collagen VII secretion by the keratinocytes are expressed in optical density units, from which the control extract of the assay is subtracted (denoted by OD—blank). These values are adjusted for the amount of cellular proteins in the corresponding well (for 72 h of incubation).

The activity of the product is evaluated by the percentage stimulation: [(collagen VII in treated NHK—collagen VII in control NHK)/collagen VII in control NHK]×100

The results obtained on the treated and control cultures are compared by the unpaired Student test, the chosen significance level being $p<0.05$.

Results—Conclusion

The results are given in Table IV below on the basis of the mean of the measurements on the different cultures:

TABLE IV

| Product and concentration | Collagen VII (OD)/ 100 μg proteins | % activity | Significance |
|---|---|---|---|
| DMSO control | 0.324 ± 0.03 | | |
| $I_3$ 1 μg/ml | 0.522 ± 0.056 | +61 | s |
| $I_3$ 2.5 μg/ml | 0.603 ± 0.155 | +86 | s |
| $I_3$ 5 μg/ml | 0.656 ± 0.116 | +102 | s | s = significant (Student test, p < 0.05)

These results clearly show that the extract of *Bertholletia excelsa* $I_3$ very strongly stimulates the synthesis of collagen VII, the main constituent of the anchoring fibrils. Thus extracts of Bertholletia can therefore advantageously be used in cosmetic or dermatological compositions or cell culture media for improving the epidermal-dermal junction.

EXAMPLE 15
Demonstration of the Effect on the Transport of Ascorbic Acid 15.1. Materials and Methods a. Origin of the Fibroblasts The cultures of normal human fibroblasts (NHF) are obtained by the explant method from surgically removed samples of healthy skin. The study involved a strain of fibroblasts originating from a face-lift carried out on a 53-year-old Caucasian woman.

b. Culture Conditions

The fibroblasts are cultivated in E199 medium (GIBCO) complemented with 2 mmol/l of L-glutamine (denoted by E199c) and with 10% v/v of fetal calf serum (GIBCO), denoted by FCS. The strain of fibroblasts used was at the primary culture stage.

c. Preparation of the Stock Solutions of Products

The methanolic extract of the pericarp of nuts of *Bertholletia excelsa*, coded $I_3$, obtained in Example 2, was tested blind by comparison with its solubilization excipient. Stock solutions of the extract at concentrations of 5, 2.5 and 1 mg/ml in dimethyl sulfoxide (DMSO) were prepared immediately before use. Each stock solution was introduced into the cell incubation medium at a concentration of 0.1% v/v to give final concentrations of 5, 2.5 and 1 μg/ml in contact with the cells. These concentrations exhibit no cytotoxicity on NHF as determined by the XTT test based on measurement of the activity of the mitochondrial succinate dehydrogenase.

d. Fibroblast Treatment Conditions 130,000 NHF per well are inoculated into an E199C medium+10% FCS in microtiter plates (24 wells, FALCON).

After incubation for 24 h, the medium is replaced with an E199C medium without FCS, to which the test product has been added at the indicated concentrations or to which the excipient for these products has been added (DMSO at 0.1% v/v). Controls without DMSO were also prepared in order to verify the absence of an inherent effect of this product on the cellular function studied.

After 48 hours of incubation, the experiment on the intracellular transport of vitamin C is performed using the sodium salt of labeled vitamin C (sodium $^{14}$C-L-ascorbate).

e. Conditions of Study of the Transport of $^{14}$C-L-ascorbic Acid into the Fibroblasts The wells are rinsed with serum-free E199C medium at 37° C. and 0.5 ml of this same medium containing 150 μmol/l of sodium $^{14}$C-ascorbate (Amersham ref.: CF620, specific activity of 14.1 Ci/μmol), prepared immediately before use, is added.

The plates are then incubated for 2 hours at 37° C., after which the incubation medium is withdrawn and the cellular mat is rinsed with serum-free medium to remove all trace of extracellular radioactivity. 500 μl/well of 60% methanol are then added to render the plasmic membrane of the fibroblasts permeable and release the intracellular contents. The 500 μl recovered, containing the intracellular $^{14}$C-ascorbate, are concentrated 10-fold and analyzed by HPLC.

f. Protein Assay

The proteins are assayed by the BCA (bicinchoninic acid, Sigma) method on the mat of cells which have been rendered permeable in each well, after solubilization with 0.1 M sodium hydroxide. The OD read off at 570 nm are converted to ng of proteins with the aid of a calibration range of bovine serum albumin (Sigma). This value makes it possible to express the amount of ascorbate per μg of proteins.

g. Assay of $^{14}$C-ascorbate by HPLC

The cellular $^{14}$C-ascorbate is identified by its retention time, which is identical to that of the initial $^{14}$C radioactive source. Quantification is effected using a radioactivity detector (Berthold) by integration of the corresponding peak.

The column used is a silica-NH$_2$ column protected by a guard column packed with the same phase. The eluent is composed of 75% (v/v) gradient grade acetonitrile (Merck) in a phosphate buffer at pH 5.95.

The total radioactivity count for intracellular+ extracellular contents is about 95%.

h. Expression of the Results and Statistical Interpretation

The intracellular amounts of $^{14}$C-ascorbate (denoted by $^{14}$C-Asc) are expressed in pmol per μg of proteins after incubation for 2 h. A complementary calculation for expressing the activity of the product (in %) was performed as follows:

$$\left( \frac{^{14}\text{C-Asc in treated NHF} - {}^{14}\text{C-Asc in control NHF}}{^{14}\text{C-Asc in control NHF}} \right) \times 100$$

The results obtained on the treated and control cultures are compared by the unpaired Student t test. The p values obtained are shown in the Tables of results below; p=0.05 is set as the significance level.

15.2. Results

The properties of the methanolic extract I$_3$ were verified by testing at three concentrations and working with 6 control cultures and 6 treated cultures.

The absence of an inherent effect of DMSO, the solubilization excipient for the extract, on the parameters measured was verified beforehand.

a. Effect of DMSO on the Transport of $^{14}$C-ascorbate

The effect of DMSO on the ascorbate is shown in Table V below:

TABLE V

| | Intracellular content of $^{14}$C-ascorbate | | |
|---|---|---|---|
| Cell treatment | Intracellular ascorbate pmol/μg prot/2 h | % activity | Significance (*) |
| Control | 1.51 ± 0.46 | | |
| +0.1% of DMSO | 1.71 ± 0.17 | (no significant effect) | NS (p = 0.541) |

* Comparison made between 3 control cultures and 3 treated cultures
NS = not significant (Student test, level: p < 0.05)

Conclusion: DMSO at 0.1% v/v does not significantly modify the intracellular content of $^{14}$C-ascorbate.

b. Effect of the Extract I$_3$ on the Transport of $^{14}$C-ascorbate

Table VI below gives the results obtained in the case of treatment with the extract I$_3$ in DMSO solution.

TABLE VI

| | Intracellular content of $^{14}$C-ascorbate | | |
|---|---|---|---|
| Cell treatment | Intracellular ascorbate pmol/μg prot/2 h | % stimulation | Significance (*) |
| +0.1% of DMSO | 1.51 ± 0.34 | | |
| I$_3$ 1 μg/ml | 2.35 ± 0.45 | +55 | S (p = 0.005) |
| I$_3$ 2.5 μg/ml | 2.30 ± 0.36 | +52 | S (p = 0.003) |
| I$_3$ 5 μg/ml | 2.69 ± 0.12 | +78 | S (p = 0.001) |

S: significance (Student test, level: p < 0.05)
* Comparison made between 6 control cultures and 6 treated cultures Conclusion This experiment clearly shows the increase in the intracellular content of $^{14}$C-ascorbate in the cells treated with the extract I$_3$ (Table VI). This increase is substantial (+55%) as from a concentration of 1 μg/ml and is statistically significant (p=0.005). At concentrations of 2.5 and 5 μg/ml, the extract I$_3$ also significantly increases (p=0.003 and p=0.0001 respectively) the intracellular content of $^{14}$C-ascorbate (52% and 78% respectively), the maximum effect occurring at a concentration of 5 μg/ml.

Thus extracts of Bertholletia very appreciably promote the incorporation of vitamin C into the fibroblasts.

EXAMPLE 16

Cosmetic Care Composition for Combating Skin Relaxation

| | | |
|---|---|---|
| Methanolic extract of Bertholletia excelsa nut pericarp (Example 2) | | 0.2 g |
| Asiaticoside | | 3 g |
| Vitamin A palmitate | | 0.01 g |
| Parsol MCX ® | | 5 g |
| Wheat protein extract | | 2 g |
| Perfumed penetrating excipient as an oil-in-water emulsion | qsp | 100 g |

This composition combats the relaxation of the skin and restores its firmness. When applied to the bust areas, it tightens the tissues and gives them a more attractive appearance after six weeks of daily treatment.

EXAMPLE 17

Anti-wrinkle Tightening Gel for the Face

| | |
|---|---|
| Extract of Bertholletia excelsa (Example 1) | 0.3 g |
| Vitamin A palmitate | 0.06 g |
| Vitamin E acetate | 0.1 g |

-continued

| Lactic acid | | 1.5 g |
| --- | --- | --- |
| Glycolic acid | | 0.2 g |
| Ethanol | | 5 g |
| Gel excipient | qsp | 100 g |

This gel can be applied locally to the neck and forehead areas with massage until it has completely penetrated. After six weeks the skin is less wrinkled and has more tonicity. It has a finer grain and the face is more radiant.

EXAMPLE 18
Treating Make-up Foundation

| Aqueous extract of Bertholletia excelsa nut pericarp (Example 13) | | 0.3 g |
| --- | --- | --- |
| Extract of Centella asiatica | | 0.2 g |
| Wheat ceramides | | 0.2 g |
| Wheat proteins | | 3 g |
| Fluid colored excipient | qsp | 100 g |

This treating make-up contributes immediately to a perceptible tightening effect and also acts deep down on the treated areas which tend to relax.

EXAMPLE 19
Dermatological Emulsion

| Extract of Bertholletia excelsa (Example 1) | | 0.5 g |
| --- | --- | --- |
| Ascorbyl palmitate | | 0.5 g |
| Emulsified excipient without perfume | qsp | 100 g |

This dermatological preparation may be applied locally to the areas to be treated in the case of epidermolysis bullosa. Clear clinical signs of improvement will appear. However, this composition must only be used on prescription and under strict medical supervision.

What is claimed is:

1. A cosmetic or pharmaceutical composition comprising as active ingredient a Bertholletia extract in a cosmetically or pharmaceutically effective amount, in a cosmetically or pharmaceutically acceptable excipient intended for topical use.

2. A composition according to claim 1, wherein said extract is extracted from *Bertholletia excelsa.*

3. A composition according to claim 1, wherein said Bertholletia extract is extracted from a part of Bertholletia selected from the group consisting of bark, nut, trunk bark and nut pericarp.

4. A composition according to claim 1, wherein said extract is obtained by extraction with a polar solvent.

5. A composition according to claim 4, wherein said polar solvent is selected from the group consisting of water, alcohols, chlorinated solvents, organic esters, and mixtures thereof.

6. A composition according to claim 4, wherein said polar solvent is selected from the group consisting of water, methanol, ethanol and mixtures thereof.

7. A composition according to claim 1, wherein said extract is enriched in saponins.

8. A composition according to claim 1, wherein said extract is present in an amount between 0.0001% and 1% by weight, based on the total weight of said composition.

9. A composition according to claim 1, further comprising an active substance selected from the group consisting of ascorbic acid, madecassic acid, asiatic acid, madecassoside, asiaticoside, alpha-1-proteinase inhibitors, collagenase inhibitors, elastase inhibitors, lysine, proline, 2-oxoglutarate, ginsenoside Ro, vitamin D, vitamin D derivatives, ecdysteroids and vitamin E.

10. A composition according to claim 1, further comprising vitamin C or a derivative thereof.

11. A method of treatment of the human body comprising the topical application to an external area of the human body of a cosmetic or pharmaceutical composition comprising a cosmetically or pharmaceutically effective amount of a Bertholletia extract.

12. A method according to claim 11, wherein said extract is extracted from *Bertholletia excelsa.*

13. A method according to claim 11, wherein said extract is present in said composition at a concentration comprised between 0.0001% and 1% by weight, based on the total weight of the final composition.

14. A method according to claim 11, wherein said method of treatment is selected from the group consisting of methods for stimulating the synthesis of collagen I, collagen IV, or collagen VII, methods for obtaining an anti-free radical activity, methods for improving skin healing as well as biochemical properties and surface appearance of the skin, methods for obtaining firmer skin, methods for combating the effects of skin ageing, methods for treating the diverse pathological conditions accompanied by a collagen deficiency, and methods for promoting the incorporation of vitamin C into the skin cells.

15. A method according to claim 11, wherein said treatment is selected from the group consisting of treatments against skin ageing, treatments against wrinkles, and treatments intended for reducing wrinkle depth.

16. A method according to claim 11, wherein said treatment is a treatment for treating pathological conditions associated with the deficiency of the epidermal-dermal junction.

17. A method according to claim 16, wherein said treatment is a treatment of epidermalysis bullosa.

18. A method according to claim 11, wherein said treatment is for treating pathological conditions associated with a deficiency of incorporation of vitamin C into the skin cells.

19. Medium for the culture of skin cells containing a Bertholletia extract in an amount sufficient for stimulating collagen synthesis by said cells or for promoting incorporation of vitamin C into said cells.

* * * * *

UNITED STATES PATENT AND TRADEMARK OFFICE
CERTIFICATE OF CORRECTION

PATENT NO. : 6,004,568
DATED : December 21, 1999
INVENTOR(S) : FREDERIC BONTE et al It is certified that error appears in the above-indentified patent and that said Letters Patent is hereby corrected as shown below:

On the title page:

Under "[30] Foreign Application Priority Data" insert:

--February 17, 1995 [FR] France 95 01840--

Signed and Sealed this

Tenth Day of October, 2000

*Attest:*

Q. TODD DICKINSON

*Attesting Officer*     *Director of Patents and Trademarks*